United States Patent [19]

Rapoport

[11] Patent Number: 5,184,078
[45] Date of Patent: Feb. 2, 1993

[54] APPARATUS FOR ROTATING AN NMR TEST TUBE

[75] Inventor: Uri Rapoport, Oak Park, Ill.

[73] Assignee: Elbit-ATI, Ltd., Oak Park, Ill.

[21] Appl. No.: 666,576

[22] Filed: Mar. 8, 1991

[51] Int. Cl.$^5$ ............................................. G01V 3/00
[52] U.S. Cl. ................................. 324/321; 324/322
[58] Field of Search ............... 324/300, 307, 316, 321, 324/322; 248/309.1, 311.2; 422/104

[56] References Cited

U.S. PATENT DOCUMENTS 3,918,920  11/1975  Barber ............................. 248/311.2
4,088,944   5/1978  Engler et al. ..................... 324/321
4,581,583   4/1986  Van Vliet et al. ................. 324/321

Primary Examiner—Louis Arana
Attorney, Agent, or Firm—Jones, Day, Reavis & Pogue

[57] ABSTRACT

Apparatus for rotating a test tube in an NMR device which allows sufficient frictional force to be applied to the test tube to rotate it at a desired speed and which allows the test tube to be inserted in and removed from the NMR device while the motor is rotating.

14 Claims, 1 Drawing Sheet

APPARATUS FOR ROTATING AN NMR TEST TUBE

FIELD OF THE INVENTION

The invention relates in general to nuclear magnetic resonance testing of a sample to determine constituents therein and in particular to the rotation of a test tube containing a sample that is to be tested for constituents with an NMR device.

BACKGROUND OF THE INVENTION

Nuclear magnetic resonance testing of substances to determine the constituents therein is well known in the art. In known devices, the sample is arranged between the poles of a magnet and is enclosed by a wire coil to enable a sample to be subjected to RF electromagnetic pulses of a predetermined frequency. The resulting NMR pulse generated by the nuclei of the sample under test is detected and processed by the NMR device in a well known manner to identify the sample constituents.

In some cases, it is important to determine the constituents of a fluid sample. In such cases, the fluid sample may be placed in a test tube and the test tube placed in the magnetic field in order to subject it to the pulsed electromagnetic field. If the sample in such cases is positioned in a magnetic field in a gap between magnet poles, small spacial nonlinearities in the magnetic field in the gap may distort the signal that is detected. One well known way of avoiding this distortion is to rotate the sample about an axis that is substantially perpendicular to the direction of the magnetic field in the gap. This, in effect, subjects the sample to the spacial average of the magnetic field provided that angular velocity of rotation of the sample is higher than the Larmor radian frequency of the charged particle that is being subjected to analysis in the given magnetic field. One method of rotating the test tube in the prior art is to use an O-ring to couple the test tube to a motor. The motor can then be controlled to rotate the test tube at a desired speed. However, the frictional engagement of the O-ring with respect to the test tube creates problems. If for any reason, resistance is applied to the test tube while it is rotating, the frictional engagement of the O-ring is sufficient to break the test tube. Also, if it is desired to remove the test tube for any reason, the motor must be stopped in rotation because if the test tube were attempted to be removed during rotation, the frictional engagement would again be sufficient to shatter the test tube. In order to avoid these problems, air bearings have been used which allow the test tube to be held in a unit that is rotated by air. It therefore allows the test tube to be removed during rotation. However, it has other disadvantages since it is affected by rotational friction and by the magnetic field in which the test tube is positioned. Further, the speed of rotation of the test tube cannot be accurately adjusted with this air bearing device.

The present invention overcomes the disadvantages of the prior art by enabling a variable speed electric motor to rotate the test tube in such a manner that the operator is permitted to grasp the spinning test tube and remove it from the unit without stopping the driving motor. It is also possible to insert a test tube into the unit while the motor is rotating to bring the test tube up to speed without breaking it. Further, the drive motor can be accurately controlled in rotational speed to cause the test tube to be rotated at any desired speed.

Thus, it is an object of the present invention to provide frictional coupling between an electric motor and a rotating test tube such that the test tube can be inserted in and removed from the rotational unit while it is being operated.

It is also an object of the present invention to utilize multiple point frictional contact between the test tube and the driving device such that the friction necessary to rotate the test tube can be generated and yet enable the test tube to be removed from and inserted in the device while it is rotating.

It is yet another object of the present invention to utilize a coil spring formed in a 360° continuous circle as a frictional engagement device rotating with the driving device and frictionally engaging the test tube.

It is also an object of the present invention to utilize a rotating brush having bristles arranged to circumferentially contact the test tube in frictional engagement to rotate the test tube.

It is still another object of the present invention to provide a frictional engagement between a rotating device and a test tube that can be adjusted to a desired degree of frictional engagement.

SUMMARY OF THE INVENTION

Thus the present invention relates to apparatus for rotating a test tube containing a sample at a predetermined rotational speed in a magnetic field in an NMR apparatus comprising a motor, a hollow shaft being driven by said motor, means for coupling the test tube to the hollow shaft with sufficient force to rotate the test tube with the rotation of shaft while allowing the test tube to be removed from and inserted in the hollow shaft while the shaft continues to rotate, and means coupled to the motor for operating the motor at a predetermined rotational speed.

The invention also relates to a method of rotating a test tube containing a sample at a predetermined rotational speed in a magnetic field in an NMR apparatus comprising the steps of rotating a hollow shaft with a motor, coupling the test tube to the hollow shaft with sufficient force to turn the tube with the shaft while allowing the tube to be inserted in and removed from the hollow shaft during rotation thereof, and operating the motor at a predetermined rotational speed.

BRIEF DESCRIPTION OF THE DRAWINGS

These and other objects of the present invention will be more fully understood in conjunction with the accompanying drawings in which like numbers indicate like components and in which.

DETAILED DESCRIPTION

Figure 1:
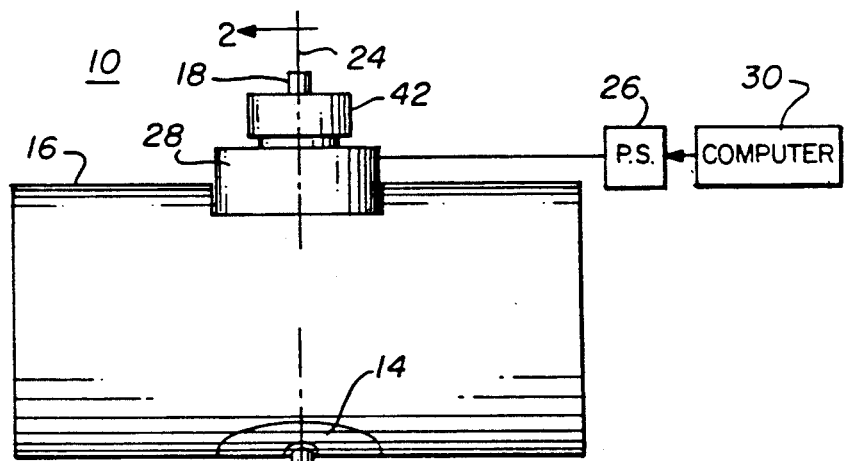
FIG. 1 is an a side view of the apparatus of the present invention.
Figure 2:
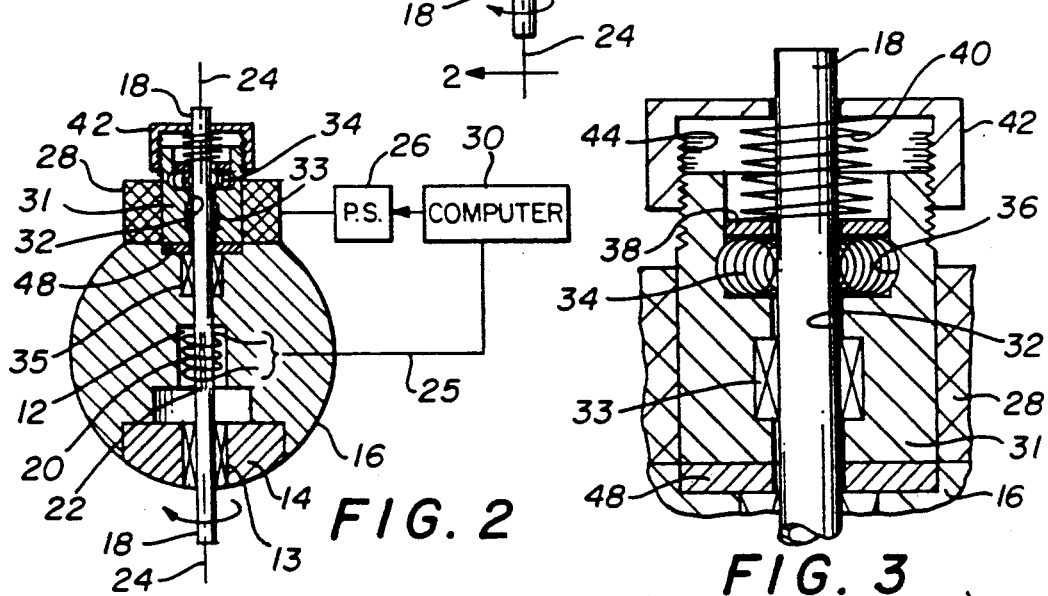
FIG. 2 is a cross sectional view of the apparatus shown in FIG. 1.

FIG. 1 is generally a side view of the apparatus for practicing the present invention. In FIG. 1, a device generally designated by the numeral 10 includes a magnet that produces a static magnetic field that is extremely linear as a function of distance in a gap 12 (shown in FIG. 2). The magnet may be of the type disclosed in commonly assigned co-pending application Ser. No. 277,209 filed Nov. 29, 1988 and incorporated herein by reference in its entirety. The magnet is shown here as including a permanent magnet 14 and a ferromagnetic armature 16, although the permanent magnet 14 could be replaced by an electromagnet without affecting the operation of the present invention. The gap 12, shown in FIG. 2, is shaped to fit a structure having cylindrical symmetry such as a test tube 18. This is the preferred embodiment although samples of different types could require different shapes for the gap 12. A computer 30 controls the power supply 26 to determine the rotational speed of motor 28. Coupled to motor 28 is a rotatable hollow shaft having a cap 42 thereon which is adjustable as will be disclosed in relation to FIG. 3.

Computer 30 also couples signals on line 25 to coil 20 (shown in FIG. 2) to provide the proper RF energy to coil 20 to provide NMR operation of the device. When the nuclei of the constituents have been subjected to the RF pulse, relaxation of the dipole moments to their original positions as aligned by a magnetic field in the gap 12 produces a signal that can be analyzed to provide information about the sample 22 as is well in the art.

As has been stated earlier, if the sample 22 is fixed in position in the gap 12, slight spacial nonlinearities in the magnetic field in the gap 12 distort the signal detected by the coil 20. One well known way of avoiding this distortion is to rotate the sample about an axis 24 that is substantially perpendicular to the direction of the magnetic field in the gap 12. This can be viewed as subjecting the sample 22 to the spacial average of the magnetic field provided that the angular velocity of rotation of the sample 22 is higher than the Larmor radian frequency of the charged particle that is being subjected to analysis in the given magnetic field. The Larmor radian frequency is given by the product of the magnetic flux density and the charge-to-mass ratio of the charged particle. Rotation of the sample is produced by a motor 28 which is controlled in speed by computer 30 in the preferred embodiment in a well known manner. The motor 28 can be either a brush type or a brushless motor depending upon safety requirements and can be either an AC or a DC motor so long as it has a rotor 31 having or driving a hollow shaft 32 and can be operated at variable speeds.

Figure 3:
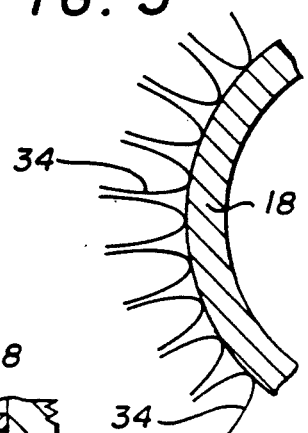
FIG. 3 is an enlarged view of the hollow shaft rotated by the motor and the frictional engagement device that couples the rotating hollow shaft to the test tube.
Figure 4:
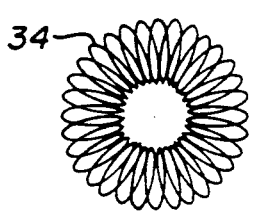
FIG. 4 is a top view of the garter spring that is used as the frictional engagement device between the hollow shaft and the test tube.
Figure 5:
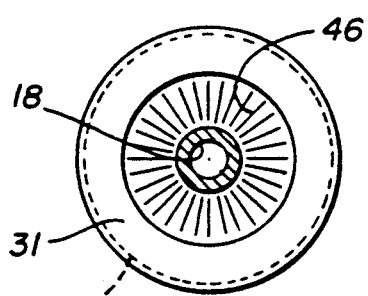
FIG. 5 is a top view of the rotatable hollow shift illustrating the radial grooves in the base of the hollow shaft to engage the garter spring shown in FIG. 4.
Figure 6:
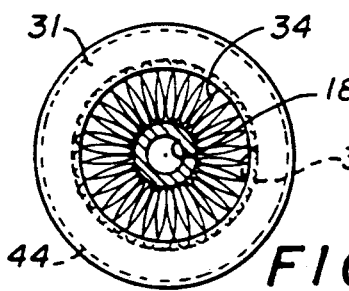
FIG. 6 is a top view of the garter spring surrounding the test tube and engaging both the test tube and the rotating hollow shaft.

FIG. 2 is a cross-sectional view of the apparatus of the present invention along lines 2—2 of FIG. 1 and FIG. 3 is an enlarged cross section of the motor 28 and its coupling to test tube 18. In FIGS. 2 and 3, the motor 28 which may be controlled by computer 30 in rotational speed, has a rotor 31 with a hollow shaft 32 that has an internal diameter slightly larger than the outer diameter of the test tube 18. A bearing surface 33, which may, for example only, be made of a self-lubricating material such as Teflon, supports the test tube 18. Bearing surface 35 in the top and bearing surface 13 in the bottom of magnet 16 may also be of a self-lubricating material such as Teflon and supports the test tube 18 for rotation in the magnet 16. The rotor 31 also rests on self lubricating bearing 48. In the preferred embodiment, a garter spring 34 is disposed in an annular groove 36 in the rotor 31. The garter spring 34 is a coiled spring formed in a 360° continuous circle as shown in FIG. 4. A groove 36 contains a portion of the garter spring 34 while permitting enough to project from the groove 36 to make frictional contact with the test tube 18 as shown in FIG. 6. This allows the application of sufficient torque to spin the test tube 18 at essentially the rotational speed of rotor 31 while permitting an operator to grasp the spinning test tube 18 and remove it from the hollow shaft 32 without stopping the motor 28 or destroying the test tube 18. It is also possible to insert the test tube 18 into the hollow shaft 32 while the rotor 31 is spinning to bring the test tube 18 up to speed without breaking it although the preferred method of spinning a test tube is to insert it into the hollow shaft 32 when the hollow shaft 32 is not spinning. A washer 38 rests on top of garter spring 34 and surrounds test tube 18. A resilient spring 40 rests on washer 38 and engages the inside of cap 42. Cap 42 has threads 44 thereon which are engaged with like threads on rotor 31. To increase the torque applied to test tube 18 by garter spring 34, the cap 42 is rotated on threads 44 to increase the pressure on spring 40. This increases the pressure on garter spring 34 by washer 38. Garter spring 34 assumes a more oval shape and increases the pressure or torque on test tube 18. In order to prevent garter spring 34 from rotating with respect to armature 31, radial grooves 46 are formed in the surface of rotor 31 on which the garter spring 34 rests as shown in FIG. 5. The individual strands of the garter spring 34 rest in the radial grooves and are retained therein and the garter spring is thus caused to rotate with the rotor 31.

Figures 7, 8:
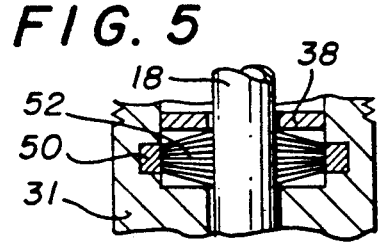
FIG. 7 is an enlarged section of the test tube and the garter spring illustrating the manner in which point contact is made by the individual strands of the garter spring against the test tube which provides sufficient frictional engagement to rotate the test tube and yet has sufficient resiliency to allow the test tube to be removed or inserted therein without breaking.
FIG. 8 illustrates an alternate form of a frictional engagement device utilizing a brush with relatively rigid bristles extending therefrom.

FIG. 7 is an enlarged view of a portion of a test tube 18 showing the contact of individual strands of garter spring 34 with the outer surface of test tube 18. It is this individual spot contact of the strands of the garter spring 34 that causes sufficient frictional engagement to rotate tube 18 but the individual strands also have sufficient resiliency to allow the tube 18 to be grasped and its rotation stopped without damaging test tube 18. Rotation of the test tube 18 containing the sample 22 produces the advantage of averaging the magnetic field in the gap 12 but it also results in the disadvantage of producing side bands in the detected signal that are a function of the angular frequency of rotation of the test tube 18. These side bands can be reduced by essentially random variation of the speed of rotation of the rotor 31. Such random variation is difficult to achieve with an air motor as used in the prior art, but is a relatively simple matter to achieve by computer control of the power supply 26 output applied to motor 28 such as a well known stepping motor. The computer 30 is readily programmed to select a sequence of speeds that is essentially random in variation in time about a predetermined average value in a well known manner. The average value of speed is relatively unimportant as long as it is above a predetermined minimum value which is the Larmor frequency of a component of the sample that is being subjected to the NMR analysis. The effect of the random variations in speed is to smear the side bands during the NMR testing and thus to cancel their effect upon the measurement of signals produced by relaxation of ions to their former positions of precessing about the static magnetic field.

The garter spring 34 may be made of spring steel, stainless steel, brass, nylon or the like. If the garter spring 34 is located sufficiently far from the coil 20 that it will not distort the magnetic fields sensed by the coil 20, the garter spring 34 may be made of a ferromagnetic materials such as spring steel. If it is desired to locate the garter spring 34 closer to the coil 20, then the garter spring 34 may be made of an electrically conducting, nonferromagnetic material such as brass or phospher bronze or it may be made of a nonmetallic substance such nylon or an engineering plastic.

In other embodiments, instead of using a garter spring, a brush 50 having bristles 52 arranged to circumferentially contact the test tube 18 as shown in FIG. 8 may also be used to locate the test tube. The brush 50 could be fixed to the rotor 31 to rotate therewith. With the bristles 52 extending from the brush in a divergent manner as shown, the washer 38 resting thereon in the manner shown in FIG. 3 could be forced by cap 42 into spring 40 against the bristles 52 thus reducing the angle of divergence and increasing the frictional engagement with the test tube 18. Other similar apparatus could be used so long as multiple point frictional contact is made between the test tube 18 and the driving device. Continual circumferential contact with test tube 18 with a device such as an O-ring makes it virtually impossible to adjust the contact pressure to allow not only rotation of the test tube but also removal of the test tube from the rotor while the rotor is turning.

Thus there has been disclosed a novel test tube spinning apparatus for use in NMR analysis. The frictional engagement between the motor and the test tube is such that the test tube can be grasped and removed from and inserted into the apparatus while the motor is operating. Further, such frictional engagement allows the use of an electric motor which can be adjusted in speed by a computer to provide needed variations in rotational speed to bring about proper analysis of the constituents in the sample being tested.

The foregoing specification describes only the embodiments of the invention shown and/or described. Other embodiments may be articulated as well. The terms and expressions used, therefore, serve only to describe the invention by example and not to limit the invention. It is expected that others will perceive differences which, while different from the foregoing, do not depart from the scope of the invention herein described and claimed. In particular, any of the specific constructional elements described may be replaced by any other known element having equivalent function.

I claim:

1. Apparatus for rotating a test tube containing a sample at a predetermined rotational speed in a magnetic field in an NMR apparatus comprising:
   a motor driving a hollow shaft in the NMR apparatus;
   friction means for flexibly and substantially circumferentially coupling the test tube to the hollow shaft with sufficient friction to rotate the test tube with the hollow shaft while allowing the test tube to be removed from and inserted in the hollow shaft during rotation of the shaft; and
   control means coupled to the motor for operating the motor at said predetermined rotational speed.

2. The apparatus of claim 1 wherein the hollow shaft is the rotor of said motor and has an internal diameter that is sufficient to allow the test tube to be rotated therein.

3. The apparatus of claim 1 wherein the motor is an electric motor.

4. The apparatus of claim 3 wherein the electric motor is a DC motor.

5. The apparatus of claim 4 wherein the control means for operating the motor comprises a computer connected to and controlling power supplied to said motor to vary the motor speed.

6. The apparatus of claim 3 wherein the means for coupling the test tube to the hollow shaft comprises;
   a garter spring disposed inside the hollow shaft surrounding, and sized to make circumferential contact with, the test tube; and
   means for holding said garter spring in position for rotation with said hollow shaft.

7. The apparatus of claim 6 wherein the means for holding the garter spring in position comprises radial grooves in at least a portion of the surface of said hollow shaft on which the garter spring rests.

8. The apparatus of claim 6 wherein the garter spring is a coiled spring formed in a 360° continuous circle.

9. The apparatus of claim 3 wherein the means for coupling the test tube to the hollow shaft comprises:
   a brush having bristles arranged to circumferentially contact the test tube, said bristles extending from the brush in a divergent manner; and
   means resting on the bristles to reduce the angle of divergence and increase the frictional engagement with the test tube.

10. Apparatus for rotating a test tube containing a sample for NMR analysis in a magnetic field in an NMR device comprising:
    an electric motor driving a hollow shaft that is substantially cylindrical about the axis of rotation, the hollow shaft being substantially equal to but sufficiently larger in diameter than the test tube to receive and allow free rotation of the test tube, the hollow shaft disposed so that its axis intersects said magnetic field;
    friction means disposed in the hollow shaft for substantially circumferentially and resiliently engaging said test tube in a frictional manner at a multiplicity of individual points such that said test tube can be grasped during rotation without damage to the test tube;
    an electric power supply coupled to said motor; and
    means connected to the power supply to control the power from the power supply to drive said motor in a predetermined pattern of speeds while rotating said test tube.

11. Apparatus as in claim 10 wherein the test tube engaging means is a garter spring disposed in an annular groove in said hollow shaft.

12. The apparatus of claim 10 wherein the predetermined pattern of rotational speeds comprises a substantially random variation in time above a predetermined minimum value.

13. The apparatus of claim 12 wherein the predetermined minimum value is the Larmor frequency of a component of the sample that is being subjected to NMR analysis in the NMR device.

14. A method for rotating a test tube containing a sample at a predetermined rotational speed in a magnetic field in an NMR apparatus comprising the steps of:
    rotating a hollow shaft in the NMR apparatus with a motor;
    coupling the test tube to the hollow shaft with flexible and substantially circumferential frictional contact to rotate the test tube with the hollow shaft while allowing the test tube to be removed from and inserted in the hollow shaft while the hollow shaft is rotating; and
    operating the motor at said predetermined rotational speed.

* * * * *